United States Patent

Ward

[11] 4,199,590
[45] Apr. 22, 1980

[54] PIPERIDINO UREAS AND THIOUREAS
[75] Inventor: Terence J. Ward, Slough, England
[73] Assignee: John Wyeth & Brother Limited, Maidenhead, England
[21] Appl. No.: 936,441
[22] Filed: Aug. 24, 1978
[30] Foreign Application Priority Data
Sep. 8, 1977 [GB] United Kingdom ............... 37567/77
[51] Int. Cl.² .................... A61K 31/38; C07D 417/12; A61K 31/445
[52] U.S. Cl. ............................... 424/267; 424/248.51; 424/248.54; 544/63; 546/208; 546/209; 546/213; 546/214; 546/267
[58] Field of Search .................. 544/63; 546/208, 209, 546/213, 214; 424/267, 248.51, 248.54
[56] References Cited
U.S. PATENT DOCUMENTS
4,061,641 12/1977 Achibald et al. ............... 260/293.61
FOREIGN PATENT DOCUMENTS
1459506 12/1976 United Kingdom .

Primary Examiner—Henry R. Jiles
Assistant Examiner—Robert T. Bond
Attorney, Agent, or Firm—Arthur E. Wilfond

[57] ABSTRACT

Compounds of formula

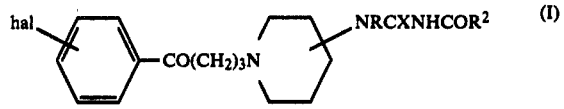

in which
hal represents halogen;
R represents hydrogen or lower alkyl having 1 to 6 carbon atoms;
$R^2$ represents a subsituted or unsubstituted monocyclic heterocyclic group;
and X represents oxygen or sulphur; or a pharmaceutically acceptable acid addition or quaternary ammonium salt thereof, are disclosed which have hypotensive and/or antihypertensive activity.

6 Claims, No Drawings

PIPERIDINO UREAS AND THIOUREAS

This invention relates to novel piperidine derivatives, to processes for their preparation and to pharmaceutical compositions containing them.

UK Pat. No. 1,459,506 discloses piperidine derivatives having the formula

and acid addition and quaternary ammonium salts thereof, wherein R represents hydrogen or lower alkyl, $R^1$ represents hydrogen, lower alkyl, cycloalkyl of 5 to 7 carbon atoms, substituted or unsubstituted aryl lower alkyl, substituted or unsubstituted aryl (including heterocyclic aryl), or substituted or unsubstituted aroyl, Ar represents a substituted or unsubstituted phenyl radical and X represents oxygen or sulphur. These compounds are disclosed as having action on the cardiovascular system, e.g. hypotensive and antihypertensive activity.

We have now found surprisingly that compounds of the above mentioned formula wherein Ar is a halophenyl group and $R^1$ is monocyclic heteroaroyl or related heterocyclic acyl group are particularly active hypotensive and/or antihypertensive agents. The compounds also show some CNS depressant activity.

Accordingly this invention provides compounds having the formula

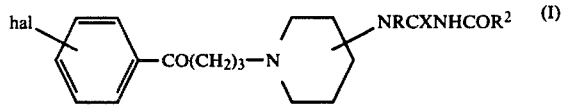

and acid addition and quaternary ammonium salts thereof, wherein hal represents halogen, R represents hydrogen or lower alkyl having 1 to 6 carbon atoms, $R_2$ represents a substituted or unsubstituted monocyclic heterocyclic group and X represents oxygen or sulphur.

Examples of hal are chlorine, fluorine and bromine. Preferably hal is fluorine. Preferably hal is in the 4-position of the phenyl. Examples of lower alkyl groups for R are methyl, ethyl, n-propyl and n-butyl. Preferably R is hydrogen. Examples of groups for $R^2$ are monocyclic heterocyclic groups wherein the heteroatom is sulphur, such as thienyl (e.g. 2-thienyl) or tetrahydrothienyl; oxygen, such as furyl (e.g. 2-furyl) or tetrahydrofuryl (e.g. 2-tetrahydrofuryl); and nitrogen, such as pyrrolyl (e.g. 2-pyrrolyl) or pyrrolidinyl. Examples of $R^2$ groups having more than 1 heteroatom are thiazolyl (e.g. 2-thiazolyl or 4-thiazolyl); thiazolinyl (e.g. 2-thiazolinyl or 4-thiazolinyl), oxazolyl (e.g. 2-oxazolyl or 4-oxazolyl), and oxazinyl (e.g. 2-oxazinyl).

Examples of substituents for the $R^2$ groups are lower alkyl of 1 to 6 carbon atoms, e.g. methyl, ethyl n-propyl, isopropyl and n-butyl and halogen, e.g. chlorine or bromine.

Preferably $R^2$ is a 5-membered heterocyclic group most preferably one containing sulphur as a heteroatom, e.g. 2-thienyl.

Preferably the —NRCXNHCOR$^2$ substituent is in the 4-position of the piperidine ring.

Examples of acid addition salts are those formed from inorganic and organic acids in particular pharmaceutically acceptable acid addition salts such as the sulphate, hydrochloride, hydrobromide, hydroiodide, nitrate, phosphate, sulphonate, (such as methane-sulphonate and p-toluenesulphonate), acetate, maleate, fumarate, tartrate and formate.

The compounds of formula (I) exhibit pharmacological activity, in particular action on the cardiovascular system, especially antihypertensive and hypotensive activity, when tested on warm blooded animals. Compounds of formula I are tested for antihypertensive activity by administering them to rats rendered hypertensive by implanting desoxycorticosterone acetate. The test procedure is:

Female rats are rendered hypertensive by implanting subcutaneously two wax pellets (30 mg) containing desoxycorticosterone acetate (15 mg) followed immediately by uninephrectomy. The drinking water is replaced by normal saline ad lib for 4 weeks. Blood pressures stabilise at a hypertensive level after 6 weeks. Systolic pressure is measured indirectly before dosing with a test compound using E and M pneumatic pulse transducer and a Devices MX2 recorder. Groups of 4 rats are dosed orally with suspensions or solutions of the test compound in 0.5% hydroxypropylmethylcellulose 0.9% saline vehicle. Blood pressures are recorded again at 2, 6 and 24 hours and the results, expressed as a percentage of the pre-dose values compared with those of a similar group of rats receiving vehicle alone.

In the above mentioned test a representative compound of this invention namely, 1-[1-(4-[4-fluorophenyl]-4-oxobutyl)-piperid-4-yl]-3-[2-thienoyl]urea, hydrochloride, one and a quarter hydrate (A) produced a marked decrease (−49.2% at 2 hours; −45.5% at 6 hours and −21.5% at 24 hours after dosing) in blood pressure in the above test at 50 mgs/kg, and smaller decreases at 25 and 10 mgs/kg.

An analogous compound within the scope of UK Pat. No. 1,459,506, namely 3-benzoyl-1-[1-(4-[4-fluorophenyl]-4-oxobutyl)piperid-4-yl]urea, in a similar test produced a less marked decrease in blood pressure (−43.4% at 2 hours; −31.0% at 6 hours and +1% at 24 hours after dosing).

The compounds of this invention were also tested for hypotensive activity by administering to normotensive anaesthetised rats. In such a test the above mentioned compound (A) produced a 30 mm Hg fall in blood pressure sustained for 15 minutes at a dose level of 0.8 mgs/kg in two rats.

This invention also includes processes for preparing the compounds of formula I. Generally these processes comprise methods analogous to those described in U.K. Pat. No. 1,459,506 mentioned hereinabove.

Accordingly this invention provides a process for preparing a compound of formula (I) as defined above which comprises reacting a compound of formula II

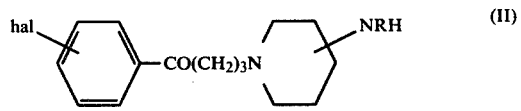

(wherein R and hal are as defined in connection with formula I) with a compound of formula III

    (III)

wherein $R^2$ is as defined in connection with formula I and X is oxygen or sulphur. This reaction should be conducted under mild conditions to avoid the possibility of reaction between the amine (II) (when R is hydrogen) and the oxobutylene radical or another molecule of amine (II) giving a Schiffs base. Usually the reaction to form the compound of formula I takes place at room temperature, in an inert solvent e.g. benzene.

The starting materials of formula II wherein R is hydrogen may be prepared by methods described in our British Pat. No. 1,345,872. The starting materials of formula II wherein R is lower alkyl may be prepared by alkylating corresponding compounds of formula II wherein R is hydrogen, or by methods analogous to those described in Brit. Specification No. 1,345,872.

The compounds of formula III may be prepared from acids of formula $R^2COOH$ by converting the acids to the acid chlorides and reacting with ammonia to form the amides. The amide is reacted with oxalyl chloride in benzene or other inert solvent to give the isocyanate. See for example: O. Tsuge, T Itoh, and S. Kanamasa, *Nippon Kagaku Zasshi*, 1968, 89, 69. (Chemical Abstracts 69, 52073v)

A second method for preparing compounds of formula I wherein X is oxygen comprises reacting a compound of formula IV

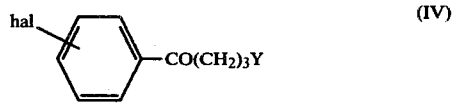

wherein hal is as defined in connection with formula I, and Y is a halogen atom, preferably chlorine or bromine, or an equivalent replaceable atom or radical for example an organic sulphonyl radical such as a tosyl radical with a compound of formula V

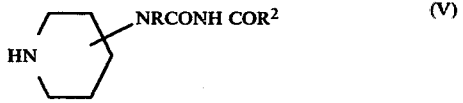

wherein R and $R^2$ are as defined in connection with formula I. This reaction may be effected under basic conditions, e.g. using triethylamine or alkali metal carbonate in isopropyl alcohol, with heating if necessary. Compounds of formula IV may be prepared as described in British Pat. No. 1,345,872. Compounds of formula (V) may be prepared by known methods, e.g. by reacting 1-benzyl-4-aminopiperidine with a compound of formula $R^2CONCX$ and hydrogenating the product to remove the benzyl group.

A further method for preparing compounds of formula (I) comprises acylating a compound of formula

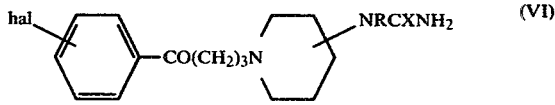

wherein hal, R and X are as defined above, using a compound of formula

wherein $R^2$ is as defined above, or a reactive derivative thereof. As examples of reactive derivatives of the acid of formula $R^2COOH$ mention is made of the halide, e.g. the chloride and the anhydride.

Generally the acid of formula $R^2COOH$ may be condensed by methods known in peptide chemistry for forming peptide bonds using a condensing agent for example a carbodiimide. In connection with the introduction of the —$COR^2$ group into a compound of formula IV, reference may be made to "Chemistry of the Amino Acids" by Greenstein and Winitz (John Wiley & Sons, Inc., Publishers, 1961) at pages 782–883 and 943–1108.

The starting materials of formula VI may be prepared by routes described in U.K. Pat. No. 1,359,506.

If necessary, in many of the aforementioned reactions, reactive substituent groups may be blocked and released at a later stage.

The invention also includes pharmaceutical compositions containing as active ingredient an active compound of formula I as above defined and a pharmaceutically acceptable carrier. The active compound may be micronised if desired ("MICRONISER" is a Registered Trade Mark). Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formation of an active ingredient with encapsulating material as carrier to give a capsule in which the active ingredient (with or without carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances, a compound is orally active and can be administered orally either in liquid or solid composition form.

Preferably the pharmaceutical composition is in unit dosage form. In such form, the composition is subdivided in unit doses containing appropriate quantities of the active ingredients; the unit dosage form can be a packaged composition, the package containing specific quantities of compositions, for example packeted powders or vials or ampoules. The unit dosage form can be a capsule, cachet or tablet itself, or it can be the appropriate number of any of these in package form. The quantity of active ingredient in a unit dose of composition may be varied or adjusted from 5 mg. or less to 500 or more, according to the particular need and the activity of the active ingredient. The invention also include the compounds in the absence of carrier where the compounds are in unit dosage form.

The following examples illustrate the invention:

EXAMPLE 1

1-{1-(4-[4-Fluorophenyl]-4-oxobutyl)piperid-4-yl}-3-[2-thienoyl]urea

A solution of 4-amino-1-(4-[4-fluorophenyl]-4-oxobutyl)piperidine (3.00 g, 0.011 mole) and 2-thienoylisocyanate (2.00 g, 0.013 mole) in sodium dried benzene (100 cm$^3$) was stirred for 12 hours. The solution was evaporated to dryness and the residue recrystallised three times from isopropylalcohol. The crystals were suspended in a little ethanol and dissolved by acidification (pH 1) with ethanolic hydrogen chloride. Ice-cooling and scratching, with addition of ether precipitated crystals of the title compound which were collected by filtration, washed with a little ether and dried to yield 1-{1-(4-[4-fluorophenyl]-4-oxobutyl)piperid-4-yl}-3-[2-thienoyl]urea, hydrochloride, one and a quarter hydrate (1.08 g) m.p. 218°–9° C.

Analysis: $C_{21}H_{24}FN_3O_3S \cdot HCl \cdot 1\frac{1}{4}H_2O$ requires C, 52.93; H, 5.82; and N, 8.82%. Found: C, 52.75; H, 5.54 and N, 8.71%.

EXAMPLE 2

1-{1(4-[4-Fluorophenyl]-4-oxobutyl)piperid-4-yl}-1-methyl-3-[2-thienoyl]urea

Using a procedure analogous to Example 1, 4-methylamino-1-(4-[4-(4-fluorophenyl)-4-oxobutyl]-piperidine is reacted with 2-thienoylisocyanate to give the title compound.

EXAMPLE 3

1-{1-(4-[4-Fluorophenyl]-4-oxobutyl)piperid-4-yl}-3-[2-furoyl]urea

Using a procedure analogous to Example 1, 4-amino-1-(4-[4-fluorophenyl]-4-oxobutyl)piperidine is reacted with 2-furoyl isocyanate to give the title compound.

EXAMPLE 4

1-{1-(4-[4-Fluorophenyl]-4-oxobutyl)piperid-4-yl}-3-[2-thiazolyl]urea

Using a procedure analogous to Example 1,4-amino-1-(4-[4-fluorophenyl]-4-oxobutyl)piperidine is reacted with 2-thiazoloyl isocyanate to give the title compound.

EXAMPLE 5

1-{1-(4-[4-Fluorophenyl]-4-oxobutyl)piperid-4-yl}-3-[2-tetrahydrothienyl]urea

Using a procedure analogous to Example 1,4-amino-1-(4-[4-fluorophenyl]-4-oxobutyl)piperidine is reacted with 2-tetrahydrothienoyl isocyanate to give the title compound.

EXAMPLE 6

1-{1-(4-[4-Fluorophenyl]-4-oxobutyl)piperid-4-yl}-3-[2-tetrahydrofuroyl]urea

Using a procedure analogous to Example 1,4-amino-1-(4-[4-fluorophenyl]-4-oxobutyl)piperidine is reacted with 2-tetrahydrofuroyl isocyanate to give the title compound.

We claim:

1. A compound of formula (I)

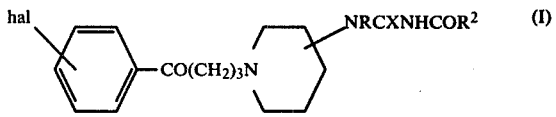

or a pharmaceutically acceptable acid addition or quaternary ammonium salt thereof, wherein hal represents halogen, R represents hydrogen or lower alkyl having 1 to 6 carbon atoms, R$^2$ represents a substituted or unsubstituted monocyclic heterocyclic group selected from thienyl, tetrahydrothienyl, furyl, tetrahydrofuryl, pyrrolyl, pyrrolidinyl, thiazolyl, oxazolyl and 1,2-oxazinyl, and the substituent is selected from the group consisting of lower alkyl of 1 to 6 carbon atoms and halogen and X represents oxygen or sulphur.

2. A compound as claimed in claim 1 wherein hal represents chlorine, fluorine or bromine in the 4 position of the phenyl ring.

3. A compound as claimed in claim 1 wherein R is hydrogen, methyl, ethyl, n-propyl or n-butyl.

4. A compound as claimed in claim 1 wherein the —NRCXNHCOR$^2$ substituent is in the 4-position of the piperidine ring.

5. A compound as claimed in claim 1 which is 1-[1-(4-[4-fluorophenyl]-4-oxobutyl)piperid-4-yl]-3-[2-thienoyl]urea.

6. A pharmaceutical composition having action on the cardiovascular system comprising an effective amount of a compound of formula I as claimed in claim 1 or a pharmaceutically acceptable acid addition or quaternary ammonium salt thereof in association with a pharmaceutically acceptable carrier.

* * * * *